United States Patent [19]
Kolias et al.

[11] Patent Number: 6,124,374
[45] Date of Patent: *Sep. 26, 2000

[54] ANTIMICROBIAL DENTURE ADHESIVE AND CLEANSER COMPOSITIONS

[75] Inventors: Fred G. Kolias, Bedminster; Eddie Wong, New Providence; Robert C. Gasman, Montville, all of N.J.

[73] Assignee: Block Drug Company, Inc., Jersey City, N.J.

[*] Notice: This patent issued on a continued prosecution application filed under 37 CFR 1.53(d), and is subject to the twenty year patent term provisions of 35 U.S.C. 154(a)(2).

[21] Appl. No.: 09/087,741

[22] Filed: May 29, 1998

[51] Int. Cl.$^7$ .............. A61K 6/00; A61K 7/00; C09K 3/00

[52] U.S. Cl. .............. 523/120; 523/118; 106/35; 424/401

[58] Field of Search .............. 523/118, 120; 106/35; 424/401

[56] References Cited

U.S. PATENT DOCUMENTS

| | | | |
|---|---|---|---|
| 2,574,476 | 11/1951 | Heath et al. | 106/207 |
| 2,745,832 | 5/1956 | Fath et al. | 260/270 |
| 2,759,838 | 8/1956 | Kolar | 106/206 |
| 2,769,006 | 10/1956 | Kalberg | 260/270 |
| 3,003,988 | 10/1961 | Germann | 260/33.6 |
| 4,280,842 | 7/1981 | Dewhirst | 106/35 |
| 4,362,510 | 12/1982 | Brauer et al. | 433/199 |
| 4,470,814 | 9/1984 | Chang et al. | 433/168 |
| 4,518,721 | 5/1985 | Dhabhar et al. | 523/120 |
| 4,569,955 | 2/1986 | Dhabhar | 523/120 |
| 4,603,152 | 7/1986 | Laurin et al. | 604/265 |
| 4,677,143 | 6/1987 | Laurin et al. | 523/122 |
| 4,694,000 | 9/1987 | Timmerman et al. | 514/187 |
| 4,725,440 | 2/1988 | Ridgway et al. | 424/465 |
| 4,725,576 | 2/1988 | Pollock et al. | 424/54 |
| 4,766,113 | 8/1988 | West et al. | 514/187 |
| 4,880,702 | 11/1989 | Homan et al. | 428/354 |
| 4,894,232 | 1/1990 | Reul et al. | 424/439 |
| 4,948,580 | 8/1990 | Browning | 424/78 |
| 4,978,391 | 12/1990 | Jones | 106/35 |
| 5,006,340 | 4/1991 | Atsuta et al. | 424/405 |
| 5,006,571 | 4/1991 | Kumar et al. | 523/120 |
| 5,116,603 | 5/1992 | Friedman | 424/49 |
| 5,154,613 | 10/1992 | Cohen | 433/228.1 |
| 5,187,124 | 2/1993 | Kweon | 501/1 |
| 5,204,414 | 4/1993 | Pelah et al. | 525/327.8 |
| 5,270,032 | 12/1993 | Pollock et al. | 424/49 |
| 5,298,017 | 3/1994 | Theenes et al. | 604/20 |
| 5,304,616 | 4/1994 | Rajaiah et al. | 526/240 |
| 5,369,145 | 11/1994 | Gasman et al. | 523/120 |
| 5,395,867 | 3/1995 | Prosise | 524/55 |
| 5,421,867 | 6/1995 | Yeager et al. | 106/18.32 |
| 5,424,058 | 6/1995 | Rajaiah et al. | 424/49 |
| 5,456,602 | 10/1995 | Sakuma | 433/215 |
| 5,575,652 | 11/1996 | Gaffar et al. | 433/173 |
| 5,714,165 | 2/1998 | Repka et al. | 424/486 |

*Primary Examiner*—Shep K. Rose
*Attorney, Agent, or Firm*—Dann Dorfman Herrell and Skillman

[57] ABSTRACT

An antimicrobial denture adhesive, denture cleansing creme or denture soaking or brushing composition comprises a combination of 8-hydroxyquinoline (or its salt) and at least one copper(II) salt. The composition fights denture stomatitis by inhibiting *Candida albicans*.

10 Claims, No Drawings

ANTIMICROBIAL DENTURE ADHESIVE AND CLEANSER COMPOSITIONS

BACKGROUND OF THE INVENTION

1. Field of the Invention

The invention relates to antimicrobial compositions for use in controlling the growth of microorganisms in the oral cavity and on dental prostheses. The antimicrobial compositions of the invention are useful as denture adhesives and as denture cleansing creams or soaking compositions. The invention also relates to methods for making and using such antimicrobial compositions.

2. Description of Related Art

Dentures and dental plates function as a substitute for missing teeth in the mouth. While dentures are usually carefully fitted for the user, the fit can change over time, causing discomfort and slippage. To alleviate the discomfort and to control the slippage, a denture adhesive may be applied to the denture. Denture adhesives usually comprise water swellable gums and/or polymers suspended in oils and petrolatum. The gums and/or polymers hydrate and become tacky when introduced to the saliva in the oral cavity, thus holding the dentures in place. Oils and petrolatum are traditionally used in the composition to avoid the premature washing away of the adhesive actives due to the constant flow of saliva through the oral cavity.

*Candida albicans* is one species of bacteria known to cause denture stomatitis, which is a serious infection of the oral mucosa. Denture stomatitis generally develops due to poor-fitting dentures or poor denture cleanliness. Normally, mucosal infections are not a problem since natural substances found in the saliva act to inhibit bacterial and fungal growth. Dentures however, are known to prevent saliva from getting to and contacting the mucosal surfaces beneath the denture. Without the presence of saliva to wash the mucosal surface under the denture, bacterial species such as *C. albicans* can flourish and cause disease.

To control bacterial growth, many different approaches have been tried. Dentifrices have been combined with antibacterial agents such as Triclosan, and mouthwashes and oral rinses, such as Listerine® mouthwash, advertise effectiveness in killing germs. Unfortunately, dentifrices and mouthwashes do not solve the problem of denture stomatitis. The dentures can still prevent saliva from reaching the oral mucosa during use, and *C. albicans* can still flourish.

Others have tried to incorporate antimicrobial agents into denture adhesives to inhibit growth of *C. albicans* and prevent stomatitis. Unfortunately, as shown below, many antimicrobial agents known to be effective against *C. albicans* have been tested and have failed to show any significant efficacy in a denture adhesive against *C. albicans*. Without wishing to be bound by theory, it appears that these antimicrobial agents may have been deactivated or sequestered in the matrix of the denture adhesive. There is still a strong need in the art for antimicrobial agents that can remain effective against *C. albicans* in a denture adhesive while retaining acceptable adhesive and organoleptic qualities.

Denture adhesive compositions and denture creams are well known in the art. U.S. Pat. No. 5,424,058 to Rajaiah et al., for example, discloses denture stabilizing compositions comprising the mixed partial salts of a lower alkyl vinyl ether/maleic acid copolymer (AVE/MA). U.S. Pat. No. 4,518,721 to Dhabhar et al. is directed to a hydrophilic denture adhesive consisting of sodium carboxymethyl cellulose and poly(oxy) ethylene oxide in a hydrophilic vehicle. The salts discussed in that patent include zinc and strontium. The AVE/MA copolymer is preferably combined with a second co-adhesive selected from the group consisting of natural gums, saccharide and cellulose derivatives and mixtures thereof. U.S. Pat. No. 5,395,867 to Prosise et al. is directed to denture adhesives with extended holding power comprising the mixed calcium, sodium, strontium, zinc, magnesium and potassium salts of the AVE/MA copolymer together with a non-cross linked non-ionic guar gum in an oil base carrier.

U.S. Pat. No. 5,369,145 to Gasman et al. teaches a denture adhesive composition comprising carboxymethyl cellulose and a partially neutralized sodium salt of AVE/MA copolymer that is further crosslinked with zinc and, optionally, other cations. The denture adhesive provides strong adhesion and bonding properties and is rapidly hydrated when applied in the oral cavity. Other denture adhesive compositions comprising mixed salts of a lower alkyl vinyl ether/maleic acid or maleic anhydride copolymers are disclosed in U.S. Pat. Nos. 5,304,616 to Rajaiah et al., 5,204,414 to Pelah et al., and 5,006,571 to Kumar et al. U.S. Pat. No. 4,470,814 to Chang also teaches a neutralized cross-linked polyacrylic acid and a hydrophilic polymer such as carboxymethyl cellulose or hydroxy propyl guar gum. None of these adhesives, however, are asserted to have antimicrobial or antibacterial properties.

Many efforts have been directed to antimicrobial compositions in the oral cavity. U.S. Pat. No. 5,403,579 to Michaels et al., for example, is directed to compositions for enhancing oral hygiene consisting of an antimicrobial compound comprising a higher alkyl-N-sulfobetaine together with a high alkyl N,N-dimethylamine oxide in a carrier base, which is formulated with other ingredients as an antiseptic mouthwash or toothpaste. These mouthwashes and toothpastes reduce plaque, calculus, bad breath and cavities.

U.S. Pat. No. 5,006,340 to Atsuta et al. is directed to a curable tooth restoration polymer that can act as a sustained release carrier for an antimicrobial agent. A polymerization initiator and other fillers react to harden and repair damaged enamel, and the polymer slowly releases the bactericidal agent to prevent or retard growth of microflora in the mouth.

The use of antimicrobial agents generally is well known. U.S. Pat. No. 4,766,113 to West et al., for example, discloses the use of copper hydrate together with 8-hydroxy quinoline as a broad spectrum antimicrobial agent in agricultural and mammalian veterinary applications and for human use as well. U.S. Pat. No. 4,694,000 to Timmerran et al. discloses biocidal quinzoline and isoquinoline derivatives including copper complexes thereof. U.S. Pat. Nos. 2,745,832 to Roth et al. and 2,769,006 to Kalberg disclose metal quinolates such as 8-hydroxy quinoline and copper, calcium and magnesium salts thereof as useful fungicidal actives.

One expired patent, U.S. Pat. No. 2,574,476 to Heath et al., discloses an antiseptic dental plate adhesive to control bacteria that cause bad breath. The adhesive comprises 8-hydroxy quinoline as the active antimicrobial in an oil and petrolatum base. U.S. Pat. No. 3,003,988 to Germann et al. also discloses the use of 8-hydroxyquinoline as an antibacterial agent in a denture adhesive.

SUMMARY OF THE INVENTION

The principal object of the present invention therefore is to provide a denture adhesive cream, denture cleanser cream, or denture soaking cleanser that significantly reduces the population of *Candida albicans* in the mouth. Preferably,

*C. albicans* should be reduced by at least 99.9% at the oral mucosa/denture interface to provide relief to denture wearers who suffer from denture stomatitis.

An advantage of the invention is that the antimicrobial agents incorporated in the denture adhesive of the invention do not interfere with the adhesive and cohesive properties of the denture adhesive. The agents also do not adversely affect the organoleptic qualities of the denture adhesive.

Additional objects and advantages of the invention will be set forth in part in the description that follows, and in part will be obvious from this description, or may be learned by practice of the invention. The objects and advantages of the invention may be realized and attained by means of the instrumentalities and combinations particularly pointed out in the appended claims.

To achieve the foregoing objects and following the purpose of the invention, as embodied and broadly described herein, the invention provides a superior, long-lasting denture adhesive that contains an antimicrobial agent. The agent is released over time for the prevention of denture stomatitis and other conditions caused or exacerbated by the presence of unwanted microorganisms in the mouth. More particularly, it is an object of the present invention to provide a denture adhesive with superior, long-lasting strength and hold that comprises 8-hydroxy quinoline and copper (II) salts, which together are extremely effective against a common but harmful micro-organism, *Candida albicans*.

To achieve the foregoing objects and following the purpose of the invention, as embodied and broadly described herein, the invention provides a superior, long-lasting denture adhesive that contains an antimicrobial agent. The agent is released over time for the prevention of denture stomatitis and other conditions caused or exacerbated by the presence of unwanted microorganisms in the mouth. More particularly, it is an object of the present invention to provide a denture adhesive with superior, long-lasting strength and hold that comprises nystatin, which is extremely effective against *C. albicans*.

Denture adhesives in accordance with the invention may be formulated as creams, powders or liners. The invention may also comprise cleaning formulations, such as effervescent tablets, liquids, soaking solutions, wipes and dentifrice-type creams and gels. Cleaning agents, however, do not provide the continuous benefits of adhesives.

To achieve the foregoing objects and purpose of the invention, the invention further provides a method for treating the oral mucosa comprising the step of administering to dentures, and thereby the oral mucosa, a composition that releases an antimicrobial agent selected from the group consisting of nystatin and a combination of 8-hydroxy quinoline and at least one copper (II) salt.

DESCRIPTION OF THE PREFERRED EMBODIMENTS

Reference will now be made in detail to the presently preferred embodiments of the invention.

This invention relates to a new antimicrobial denture adhesive, denture cleansing cream, or denture soaking or brushing cleanser composition designed to be effective in reducing the population of *Candida albicans*. *C. albicans* is the primary microorganism responsible for the most commonly encountered intraoral abnormality among denture users, denture stomatitis. This composition is able to slowly release the active ingredient, which maybe nystatin or a combination of 8-hydroxyquinoline (or its salts) and at least one copper (II) salt, from the oil-based vehicle of the adhesive composition.

The invention not only provides superior bonding and adherent properties to fasten the denture to the oral mucosa of the wearer securely, but also provides a long lasting, sustained release of an antimicrobial agent to the area defined by the underside of the denture and the mucosal surface. This antimicrobial action is particularly effective against *Candida albicans* which is the bacteria largely, if not solely, responsible for the oral condition known as denture stomatitis.

The active antimicrobial ingredient in the adhesive composition of the present invention may be the combination of a of 8-hydroxy quinoline or its salt, such as 8-hydroxyquinoline sulfate, 8-hydroxyquinoline citrate, and 8-hydroxyquinoline benzoate, and copper(II) compounds, including, but not limited to, copper(II) chloride, copper(II) sulfate, copper(II) acetate, copper(II) bromide, copper(II) carbonate, copper(II) fluoride, copper(II) gluconate, copper (II) hydroxide, copper(II) hydroxide phosphate, copper(II) methoxide, copper(II) nitrate, copper(II) oxide, copper(II) perchlorate, copper(II) sulfide and any hydrated forms of the aforementioned copper(II) compound.

The 8-hydroxyquinoline or its salt may comprise any amount of the denture adhesive or other delivery system that is effective in inhibiting growth of *C. albicans* or other microorganism in combination with a copper(II) salt. Preferably, however the 8-hydroxyquinoline or its salt comprises from about 0.0001% to about 0.5% by weight or its salt may comprise from about 0.001% to about 0.3% by weight of the denture adhesive and most preferably from about 0.01% to about 0.1% by weight of the denture adhesive.

Likewise, the copper(II) salt may comprise any amount of the denture adhesive or other delivery system that is effective in inhibiting growth of *C. albicans* or other microorganism in combination with 8-hydroxyquinoline (or its salts). Preferably, the copper(II) salt comprises from about 0.0001% to about 1% by weight of the denture adhesive. More preferably the copper (II) salt comprises from about 0.001% to about 0.1% by weight of the denture adhesive and most preferably from about 0.01% to about 0.06% by weight.

Together, the combined ingredients may comprise any amount of the denture adhesive or other delivery system that is effective in inhibiting growth of *C. albicans* or other microorganism. Preferably, the combined ingredients comprise from about 0.0001% to about 2.0% by weight of the denture adhesive, preferably 0.001% to about 1.0% by weight, and more preferably from about 0.01% to about 0.5% by weight of the denture adhesive.

The ranges for the 8-hydroxyquinoline (or its salts) and the copper(II) salts given above are for the denture adhesive creams described herein. Other delivery systems, including denture adhesive powders and liners may require different levels of materials to be effective in practice of the invention. For example, incorporation of the antimicrobial agents of the invention into an effervescent tablet denture cleanser may permit significantly higher levels of such agents to accomplish very high levels of antimicrobial activity without being concerned about organoleptic qualities of the cleaning bath made using the tablet.

8-hydroxyquinoline and copper(II) compounds did not show significant activity against *C. albicans* when incorporated individually into an oil-based denture adhesive. When combined, however, these compounds apparently form a metal complex that proves lethal against *C. albicans* when the denture adhesive is hydrated by saliva. This presumed metal complex apparently is able to diffuse from the oil phase of the adhesive vehicle into the aqueous phase and retain antimicrobial activity at the oral mucosa/denture interface.

The mode of action against various bacteria and fungi of 8-hydroxyquinoline copper salts has been well investigated. It was shown by Albert (Albert, A. et al. *British J. of Experimental Pathology*, 34(2):119–130, (1953)) that the ability of 8-hydroxyquinoline to form metal complexes with divalent metals was the main factor that determined antimicrobial activity of the compounds. Divalent metallic ions form two kinds of complexes with 8-hydroxyquinoline, a 1:1 complex in which one metallic cation is bound by chelation to only one 8-hydroxyquinoline anion, and a 1:2 complex in which the metallic ion is saturated by combination with two 8-hydroxyquinoline anions. When there is an excess of metallic ions the 1:1 complex is favored, whereas when 8-hydroxyquinoline is in excess, the 1:2 complex is favored. These two complexes differ greatly in their physicochemical properties. The 1:1 complex is positively charged, freely soluble in water and almost insoluble in lipoids and lipoid-solvents and show antibacterial activity. The 1:2 complex is electrochemically neutral, freely soluble in lipoids and lipoid-solvents, is almost insoluble in water and is devoid of antibacterial activity. Without wishing to be bound by theory, the ability of the 8-hydroxyquinoline and copper (II) salts to form two different complexes with such different properties may account for its surprising and unexpected activity.

Nystatin, on the other hand, is a well-known polyene antifungal, antibiotic complex. It has been described in the literature and its purification has been described in U.S. Pat. No. 2,832,719 to Vandeputte, and U.S. Pat. No. 3,517,100 to Renella. As stated above, this ingredient may comprise any amount of a denture adhesive or other delivery system that will be effective against *C. albicans*. Preferably, however, the nystatin comprises from about 0.0001% to about 5% by weight of the denture adhesive, preferably from about 0.001% to about 0.5% by weight and most preferably from about 0.01% by weight to about 0.05% by weight.

The salt derivatives of 8-hydroxyquinoline are incorporated into the denture adhesive or can be formulated into a denture adhesive liner, powder or liquid. These systems generally further comprise mineral oils, petrolatum, water swellable gums, and a base comprising the partial mixed salts of lower alkyl vinyl ether/maleic acid or maleic anhydride copolymers. Other ingredients may be found in these systems include a hydrophilic compound such as cellulose derivatives including carboxymethyl cellulose, hydroxypropyl methyl cellulose and the like as well as flavorants, colorants, stabilizers and flow agents such as fumed silica and the like. Liners may also include a support matrix, such as a polymeric material, that provides a base for the adhesive material.

Specifically, the mixed partial salts of the lower alkyl vinyl ether/maleic acid or maleic anhydride copolymers comprise the partial calcium, zinc, sodium, magnesium and potassium salt compounds as set forth in U.S. Pat. Nos. 5,395,867 to Prosise et al. and 5,424,058 to Rajaiah et al. both of which are incorporated by reference herein. The copolymer of the invention is preferably a vinyl alkyl ether/maleic acid or anhydride copolymer, but other polymers may be used. The preferred copolymer is a copolymer available from GAF corporation, Wayne, N.J., under the trademark "GANTREZ" in two forms: the acid form is sold under the trademark GANTREZ S Series and the preferred type of acid is identified as GANTREZ S95 or GANTREZ S97. The anhydride form is sold as the GANTREZ AN Series, and the preferred anhydride is GANTREX AN169.

Preferably, the salt comprises from about 10% to about 50% by weight of the total denture adhesive composition. More preferably, the salt comprises from about 20% to about 40% of the final denture adhesive composition and most preferably about 30% by weight of the denture adhesive composition.

The water swellable gums useful in the antimicrobial denture adhesive creams of the present invention include natural and synthetic gums such as cellulose and its derivatives, acacia gum, traganth, karaya gum, polyvinyl pyrrolidone (PVP), guar gum and its derivatives, gelatin, algins, sodium alginate and mixtures thereof.

Carboxymethyl cellulose is used in denture adhesive creams for sensitizing the adhesive to moisture, enhancing the cohesive properties of the formulation and improving gel strength. Carboxyethyl cellulose and carboxypropyl cellulose materials may also be for this purpose.

Carboxymethyl cellulose preferably comprises from about 10% to about 30% by weight of the denture adhesive composition, more preferably from about 15% to about 25% and most preferably about 24% of the composition. The carboxymethyl cellulose may be present in the form of a full or partial salt, preferably a sodium salt. During use, zinc or other divalent cations from the MVE/MA salt may replace at least some of the sodium and or crosslinks within the carboxymethyl cellulose. These cations may also replace some linkages between the cellulose and the MVE/MA salt formed during the manufacturing process.

Sodium carboxymethylcellulose is a powder which, when moistened, becomes hydrated and tacky or gummy in consistency with adhesive characteristics. The sodium carboxymethyl cellulose gums that are employed in this invention are water soluble, anionic, long chain polymers derived from cellulose.

Properties vary with the average number of carboxymethyl groups that are substituted per anhydroglucose unit in each cellulose molecule. This property is generally referred to as "the degree of substitution," with the maximum substitution possible designated as "3.0" since there are just three hydroxy groups capable of reaction in each anhydroglucose unit. For the practice of this invention, it has been found that one or more such cellulose gums having a degree of substitution of from about 0.4 to about 1.2 are suitable. The viscosity of a one percent solution of the gum, measured at 25° C., should be in the range of from about 400 to 4,500, and preferably from about 1,500 to 2,500, centipoises.

Other ingredients present in the denture adhesive include thickening agents and carriers such as petrolatum and mineral oil, flavors, colors, preservatives and non-toxic anticaking agents such as silica, magnesium stearate and talc. These ingredients, and the appropriate levels at which the ingredients should be present in a particular formulation for a specific purpose, are well known in the art.

For a cream base, the mineral oil or other carrier preferably comprises from about 10% to about 30% by weight of the denture adhesive, preferably from about 15% to about 25% by weight. Petrolatum or some other thickening agent comprises from about 15% to about 30% by weight of the denture adhesive composition preferably from about 20% to about 30% by weight.

Other nonactive ingredients comprise colorants, flavors and preservatives and may comprise up to about 10% by weight of the denture adhesive composition.

Preservatives that may be used in the denture adhesive formulations of the invention include those known agents conventionally employed in the art, such as benzoic acid and sodium benzoate; the parabens; sorbic acid and sorbates; propionic acid and the propionates; the acetic acid and acetates; nitrates and nitrites; sulfur dioxide and the sulfites. The parabens include the methyl, ethyl, propyl and butyl esters of parahydroxybenzoic acid. Methyl paraben and propyl paraben are the preferred preservatives of the invention, preferably utilized in amounts of about 0.03% to about 0.6% by weight of the total denture adhesive composition.

Sweetening agents are optionally employed and may be selected from a wide range of materials including water-soluble agents, water-soluble artificial sweeteners, and dipeptide-based sweeteners, including mixtures thereof. In general, the amount of sweetener when used will vary with the desired amount of sweetener selected for a particular denture adhesive formulation. This amount may be about 0.001% to about 5.0% by weight of the final denture adhesive composition.

Colorants may also be used in the present invention and include pigments such as titanium dioxide or dyes suitable for food, drug and cosmetic applications. Theses colorants are known as F.D. & C. dyes. The materials acceptable for the foregoing spectrum of use are preferably water-soluble. Illustrative examples include indigo dye, known as F.D. & C. Blue No. 2, which is the disodium salt of 5,5-indigotindisulfonic acid. Similarly, the dye known as F.D. & C. Green No. 1, comprises a triphenylmethane dye and is the monosodium salt of the 4-[4-N-ethyl-p-sulfobenzylamino) diphenylmethylene1 [1-N-ethyl-p-sulfobenzylamino) diphenylmethylene1-[1-N-ethyl-N-P-sulfo-benzyl)2,5-cyclohexadieniminel. Another useful colorant is F.D. & C. Red No. 3. A full recitation of F.D. & C. and D. & C. colorants and their corresponding chemical structures may be found in the Kirk-Othmer Encyclopedia of Chemical Technology, 3rd Edition in Volume 6, at pages 561–595.

Excipients may also comprise of from about 0.001% to about 5.0% by weight of the total composition.

The compositions of the present invention are manufactured in an art-recognized manner known to those skilled in the art, such as in a powder, cream, ointment, liquid, paste, liner or film. The compositions of the present invention are preferably manufactured using appropriate micronization techniques such as fluid energy, air jet or hammer milling of drum dried mixed partial salts of AVE/MA copolymer. Suitable examples of such formulations are disclosed in U.S. Pat. Nos. 4,518,721 and 4,514,528, both to Dhabhar et al. and both of which are incorporated by reference herein. The antimicrobial agent may be added at any time during the preparation process.

One advantage of the invention is that the antimicrobial compositions used in the denture adhesive creams do not lose their effectiveness. Other antimicrobials have been tried in denture adhesives and have failed. Some of those failed antimicrobials include: 2,4,4-trichloro-2-hydroxydiphenyl ether (triclosan), chlorhexidine, benzlkonium chloride, ethanol, PVP iodine, zinc salts, copper salts, stannous fluoride, hexyl resorcinol, benzyl alcohol, silver sulfadiazine, potassium benzoate, calcium propionate, sulfacetamide, quinaldic acid, L-hisidine, hexachlorophene, sodium percarbonate, menthol, methyl salicylate, eucalyptol, 8-hydroxyquinoline, 8-hydroxyquinoline sulfate, 1,10 phenathrolien, 8-mercaptoquinoline, 6-methylquinoline, 2-methylquinoline, 2-quinolinethiol, miconazole, clotrimazole, amphotericin B, and zinc undecylenate. The failure of these compositions does not appear to satisfy any consistent theory. Without being bound by theory, it seems that the agents are sequestered, neutralized or otherwise deactivated by the complex polymeric hydrated matrix found in a functioning denture adhesive.

The following examples are intended to illustrate the invention and to describe and more fully set forth how one skilled in the art may prepare specific embodiments of the invention. The examples are intended for illustrative purposes only, however, and those skilled in the art will understand that changes and/or alterations may be made that are not set forth in these examples.

EXAMPLES 1 & 2

Antimicrobial denture adhesives were prepared having the formulations set out in Table 1 in accordance with the following process: purified water was charged into a main reaction kettle equipped with a high speed stirrer. The anhydrous MVE/MA copolymer was slowly added to the main mix kettle, with continuous mixing. The batch was then heated to 85°–95° C. Water was also charged into a secondary kettle and NaOH, ZnO and MgO (all USP grade anhydrous) were added slowly. The mixture formed a slurry which was slowly added to the main reaction kettle while mixing at high speed to prevent localized reaction. The temperature was then lowered and mixing was continued. The resulting solution was poured into shallow stainless steel drying trays, and the trays were placed in a hot air convection oven at 70° C. for 18–20 hours to give a dried salt. The resulting partial salt was then combined with the other ingredients to form a denture adhesive formulation.

TABLE 1

Denture Adhesive Formulations

| Ingredient | Example 1 Weight % | Example 2 Weight % |
|---|---|---|
| MVE/MA Na, Mg, Zn Partial Salt | 30.00% | 30.00% |
| Carboxymethyl Cellulose | 24.00% | 24.00% |
| Petrolatum | 28.89% | 29.02% |
| Mineral Oil | 16.00% | 16.00% |
| 8-hydroxyquinoline citrate | 0.10% | 0.00% |
| Copper(II) sulfate pentahydrate | 0.06% | 0.00% |
| Nystatin | 0.00% | 0.03% |
| Flavorant | 0.40% | 0.40% |
| Fumed silica | 0.50% | 0.50% |
| Colorants | 0.05% | 0.05% |
| Total | 100.00% | 100.00% |

EXAMPLES 3–46

A *Candida albicans* (ATCC 10231) culture (1.0 mL) was placed in 99.0 mL of Sabouraud Dextrose broth. This suspension was shaken for 24 hours at 37° C. to allow the *C. albicans* population to grow. In a separate flask (#2), 5.0 mL of fetal calf serum was added to 95.0 mL of sterile saline solution. After the *C. albicans* was allowed to grow for 24 hours, the contents of flask #2 is added to the *C. albicans* suspension. This 200 mL of Candida solution was the inoculum used. The density of *C. albicans* of this preparation was always in the $10^7$ CFU/mL range.

A sample of the denture adhesive formulation to be tested (2 grams) was spread evenly to cover the bottom of a 100×15 mm petri dish. Twenty (20.0) inoculum were placed in the petri dish covering the adhesive sample. The petri dish was placed in a 37° C. incubator for 24 hours. After 24 hours, the sample was removed from the incubator and a 1.0 mL aliquot was taken from the surface of the adhesive. The aliquot was diluted with sterile saline solution and plated with Sabouraud Dextrose agar. The agar plates were incubated at 37° C. for 48 hours and then counts were made to determine the number of colony forming units per mL (CFU/mL).

For comparative purposes, denture adhesive formulations were prepared using different antimicrobial compounds. These were then plated on the cultures as described herein and the number of colony forming units per mL were determined. The denture adhesive formulations, were identical, except that the antimicrobial compounds were, of course, different. The antimicrobials used, and the results obtained (expressed as the log of the reduction in colony forming units), are shown in Table 2.

TABLE 2

Antimicrobials and Colony Forming Units

| Antimicrobial (wt. percent) | Log Reduction | Antimicrobial (wt. percent) | Log Reduction |
| --- | --- | --- | --- |
| 0.1% 8-hydroxyquinoline salts + 0.06% $CuCl_2.2H_2O$ | 7.20 ± 0.2 | 0.05% 8-hydroxyquinoline salts + 0.03% $CuCl_2.2H_2O$ | 2.02 ± 0.7 |
| 0.5% Miconazole | <1.0 | 0.03% Nystatin | 7.11 |
| 0.5% Ciclopirox olamine | <1.0 | 0.5% Clotrimazole | <1.0 |
| 0.5% Amphotericin B | <1.0 | 0.5% Econazole | <1.0 |
| 0.5% 5-fluorocytosine | <1.0 | 0.5% Tolnaftate | <1.0 |
| 1.0% Zinc undecylenate | <1.0 | 1.0% Dehydroacetic acid | <1.0 |
| 0.3% 2,3,3,-trichloro-2-hydroxydiphenyl ether | <1.0 | 1.0% sulfacetamide + 0.1% EDTA | <1.0 |
| 1.0% silver sulfadiazine | <1.0 | 1.0% benzyl alcohol | <1.0 |
| 2.5% calcium propionate | <1.0 | 0.66% potassium benzoate | <1.0 |
| 0.5% Sulfisoxazole | <1.0 | 3.0 % sulfacetamide | <1.0 |
| 0.3% quinaldic acid + 0.5% $CuSO_4.5H_2O$ | <1.0 | 0.5% 1,10 phenathroline + 1.26% $CuSO_4.5H_2O$ | <1.0 |
| 0.3% imidazolidinyl urea | <1.0 | 0.37% chlorhexidine diacetate | <1.0 |
| 1.0% glycerol monolaurate | <1.0 | 1.0% tea tree oil | <1.0 |
| 1.0% PVP-iodine | <1.0 | 0.05% benzalkonium chloride | <1.0 |
| 0.9% copper salts | <1.0 | 3.6% zinc salts | <1.0 |
| 0.1% hexylresourcinol | <1.0 | 0.62% stannous fluoride | <1.0 |
| 1.0% benzyl alcohol | <1.0 | 1.0% ethanol | <1.0 |
| 2.5% calcium propionate | <1.0 | 0.3% silver sulfadiazine | <1.0 |
| 1.0% L-histidine | <1.0 | 2.66% potassium benzoate | <1.0 |
| 3.0% sodium percarbonate | <1.0 | 0.1% hexetidine | <1.0 |
| 0.3% quinaldic acid | <1.0 | 0.3% hexachlorophene | <1.0 |
| 0.5% 8-mercaptoquinoline HCl + 1.26% $CuSO_4.5H_2O$ | <1.0 | 0.62% menthol, methyl salicylate, eucalyptol, thymol | <1.0 |
| 0.390% 8-hydroxyquinoline sulfate | <1.0 | 0.5% 2-methylquinoline sulfate + 1.26% $CuSO_4.5H_2O$ | <1.0 |

Denture adhesive formulations incorporating a mixture of 8-hydroxyquinoline and copper(II) salts gave far greater kill rates (7× and 2×, respectively) than the other antimicrobial compounds which either were ineffective in killing *C. albicans* or were not released from the denture adhesive to become effective.

The purpose of the above description is to illustrate some embodiments of the present invention without implying a limitation. It will be apparent to those skilled in the art that various modifications and variations may be made in the apparatus or procedure of the invention without departing from the scope or spirit of the invention.

What is claimed is:

1. An antimicrobial composition that is effective in the prevention and/or treatment of denture stomatitis consisting essentially of a denture adhesive containing an antimicrobial agent consisting of a mixture of a copper(II) salt and 8-hydroxyquinoline or a salt thereof a mixture of a copper (II) salt and 8-hydroxy quinoline or a salt thereof said denture adhesive being free from other antimicrobial agents.

2. The antimicrobial composition of claim 1, wherein said salt of 8-hydroxyquinoline is selected from the group consisting of 8-hydroxyquinoline sulfate, 8-hydroxyquinoline citrate, and 8-hydroxyquinoline benzoate.

3. The antimicrobial composition of claim 1, wherein said copper (II) salt is selected from the group consisting of copper (II) chloride, copper (II) sulfate, copper (II) acetate, copper (II) bromide, copper (II) carbonate, copper (II) methoxide, copper (II) nitrate, copper (II) oxide, copper (II) Perchlorate, copper(II) sulfide, their hydrated derivatives and mixtures thereof.

4. The antimicrobial composition of claim 1, wherein said composition further comprises the mixed partial salt of a lower alkyl vinyl ether/maleic acid or maleic anhydride copolymer (AVE/MA), a hydrophilic gum, mineral oil, vegetable oil, petrolatum, fillers, colorants, flavorants, sweeteners, silica and mixtures thereof.

5. The antimicrobial denture adhesive of claim 4, wherein said salt of 8-hydroxyquinoline is incorporated into said adhesive composition in an amount of from about 0.0001 wt % to about 1.5 wt % based on the total weight of the adhesive formulation.

6. The antimicrobial composition of claim 5, wherein said salt of the AVE/MA copolymer is selected from the group consisting of partial slats of calcium, sodium, manganese, strontium, zinc, phosphorus and mixtures thereof.

7. The antimicrobial composition of claim 6 wherein said hydrophilic gum is selected from the group consisting of cellulose and its derivatives, guar gum, karaya gum, gelatin, algin, sodium alginate, acacia gum, polyethylene oxide polymers and mixtures thereof.

8. The antimicrobial composition of claim 7, wherein said cellulose derivatives are selected from the group consisting of methyl cellulose, carboxymethyl cellulose, hydroxypropyl methyl cellulose, their salts and mixtures thereof.

9. The antimicrobial composition of claim 1, formulated as a powder, creme, gel liner, effervescent tablet, cleansing cream or liquid.

10. A method for the treatment or prevention of denture stomatitis in a human wearing dentures consisting essentially of adhering said dentures to the oral mucosa of the wearer using a denture adhesive material comprising the antimicrobial composition of claim 1.

* * * * *